(12) United States Patent
Hua et al.

(10) Patent No.: US 11,927,563 B2
(45) Date of Patent: Mar. 12, 2024

(54) SMART ACOUSTIC INFORMATION RECOGNITION-BASED WELDED WELD IMPACT QUALITY DETERMINATION METHOD AND SYSTEM

(71) Applicant: NANTONG UNIVERSITY, Nantong (CN)

(72) Inventors: Liang Hua, Nantong (CN); Ling Jiang, Nantong (CN); Juping Gu, Nantong (CN); Cheng Lu, Nantong (CN); Kun Zhang, Nantong (CN); Kecai Cao, Nantong (CN); Liangliang Shang, Nantong (CN); Qi Zhang, Nantong (CN); Shenfeng Wang, Nantong (CN); Yuxuan Ge, Nantong (CN); Zixi Ling, Nantong (CN); Jiawei Miao, Nantong (CN)

(73) Assignee: NANTONG UNIVERSITY, Nantong (CN)

( * ) Notice: Subject to any disclaimer, the term of this patent is extended or adjusted under 35 U.S.C. 154(b) by 100 days.

(21) Appl. No.: 17/288,560

(22) PCT Filed: Oct. 28, 2020

(86) PCT No.: PCT/CN2020/124189
§ 371 (c)(1),
(2) Date: Apr. 25, 2021

(87) PCT Pub. No.: WO2021/068983
PCT Pub. Date: Apr. 15, 2021

(65) Prior Publication Data
US 2022/0276204 A1    Sep. 1, 2022

(30) Foreign Application Priority Data
Nov. 8, 2019  (CN) .......................... 201911088740.4

(51) Int. Cl.
*G01N 33/207*    (2019.01)
*B23K 37/00*    (2006.01)
(Continued)

(52) U.S. Cl.
CPC .......... *G01N 29/045* (2013.01); *B23K 37/00* (2013.01); *G01N 29/46* (2013.01); *G01N 33/207* (2019.01);
(Continued)

(58) Field of Classification Search
CPC .... G01N 29/045; G01N 29/46; G01N 33/207; G01N 2291/0234; G01N 2291/0289;
(Continued)

(56) References Cited

U.S. PATENT DOCUMENTS

2018/0361514 A1*  12/2018  Narayanan ........... B23K 9/0953

FOREIGN PATENT DOCUMENTS

CN    107045718 A  *  8/2017

OTHER PUBLICATIONS

Ren et al. ("Seam Penetration Recognition for GTAW Using Convolutional Neural Network Based on Time-Frequency Image of Arc Sound," 2018 IEEE 23rd International Conference on Emerging Technologies and Factory Automation (ETFA), Turin, Italy, 2018, pp. 853-860, doi: 10.1109/ETFA.2018.8502478.) (Year: 2018).*
(Continued)

*Primary Examiner* — Manish S Shah
*Assistant Examiner* — Christian T Bryant
(74) *Attorney, Agent, or Firm* — CBM PATENT CONSULTING, LLC

(57) ABSTRACT

A smart acoustic information recognition-based welded weld impact quality determination method and system, comprising: controlling a tip of an ultrasonic impact gun (1) to perform impact treatment on a welded weld with different
(Continued)

treatment pressures, treatment speeds, treatment angles and impact frequencies, obtaining acoustic signals during the impact treatment, calculating feature values of the acoustic signals, and constructing an acoustic signal sample set including various stress conditions; marking the acoustic signal sample set according to impact treatment quality assessment results for the welded weld; establishing a multi-weight neural network model, and using the marked acoustic signal sample set to train the multi-weight neural network model; obtaining feature values of welded weld impact treatment acoustic signals to be determined, inputting the feature values into the trained multi-weight neural network model, and outputting determination results for welded weld impact treatment quality to be determined.

3 Claims, 4 Drawing Sheets

(51) Int. Cl.
| | |
|---|---|
| *G01N 29/04* | (2006.01) |
| *G01N 29/46* | (2006.01) |
| *G06N 3/08* | (2023.01) |
| *G06T 7/11* | (2017.01) |
| *H04R 1/08* | (2006.01) |
| *H04R 3/04* | (2006.01) |
| *B23K 31/00* | (2006.01) |
| *B23K 31/12* | (2006.01) |
| *G01N 29/34* | (2006.01) |
| *G01N 29/44* | (2006.01) |

(52) U.S. Cl.
CPC ............... *G06N 3/08* (2013.01); *H04R 3/04* (2013.01); *B23K 31/006* (2013.01); *B23K 31/125* (2013.01); *G01N 29/348* (2013.01); *G01N 29/4481* (2013.01); *G01N 2291/0234* (2013.01); *G01N 2291/0289* (2013.01); *G01N 2291/267* (2013.01); *G01N 2291/2675* (2013.01); *G06T 7/11* (2017.01); *G06T 2207/20084* (2013.01); *H04R 1/08* (2013.01)

(58) Field of Classification Search
CPC ........... G01N 2291/267; G01N 29/348; G01N 29/4481; G01N 2291/2675; B23K 37/00; B23K 31/006; B23K 31/125; G06N 3/08; G06N 3/02; H04R 3/04; H04R 1/08; G06T 2207/20084; G06T 7/11
See application file for complete search history.

(56) References Cited

OTHER PUBLICATIONS

Zhang et al.("Audible Sound-Based Intelligent Evaluation for Aluminum Alloy in Robotic Pulsed GTAW: Mechanism, Feature Selection, and Defect Detection," in IEEE Transactions on Industrial Informatics, vol. 14, No. 7, pp. 2973-2983, Jul. 2018, doi: 10.1109/TII.2017.2775218.) (Year: 2018).*

Lv et al.("Research on welding penetration state recognition based on BP-Adaboost model for pulse GTAW welding dynamic process," 2016 IEEE Workshop on Advanced Robotics and its Social Impacts (ARSO), Shanghai, China, 2016, pp. 100-105, doi: 10.1109/ARSO.2016.7736264.) (Year: 2016).*

* cited by examiner

SMART ACOUSTIC INFORMATION RECOGNITION-BASED WELDED WELD IMPACT QUALITY DETERMINATION METHOD AND SYSTEM

TECHNICAL FIELD

The present invention relates to the field of mechanical control, in particular to a smart acoustic information recognition-based welded weld impact quality determination method.

DESCRIPTION OF THE RELATED ART

As an indispensable part of the manufacturing industry, welding is developing from low-power, low-precision and low-quality welding to high-power, high-precision and high-quality welding. Among them, the stress treatment after welding is completed in the entire high-quality welding process. China is particularly important. The uneven temperature field after welding will lead to uneven stress distribution in the weld, thereby reducing the yield strength and fatigue strength of the weldment, and severely causing serious consequences such as weldment deformation and weld cracking.

Among the existing methods for eliminating residual stress in welds, the ultrasonic impact method is the best method. Strike technology is an efficient way to eliminate harmful residual tensile stress on the surface of the component or the weld area, and to introduce method of benefiting compressive stress. Ultrasonic impact equipment uses high-power energy to push the impact head at a rate per second the frequency of about 20,000 times impacts the surface of metal objects, and the high-frequency, high-efficiency and large energy under focus make the metal surface produces a large compression plastic deformation; at the same time, the ultrasonic impact changes the original stress field, producing beneficial compressive stress; metal surface temperature rises rapidly and rapidly under high-energy impact cooling changes the surface metal structure of the affected area and strengthens the impact site.

The processing speed, pressure, angle, steel type, thickness and other factors in the operation of the ultrasonic impact method determine the quality of the ultrasonic impact method, but these factors are difficult to measure and quantify during the operation. Because the time-frequency domain characteristics of the ultrasonic shock sound signal during operation contain a lot of information, these sound signal characteristics are a comprehensive manifestation of external factors during the operation and determine the quality of ultrasonic shock. The quality of the ultrasonic impact acting on the weldment seam directly determines the degree of residual stress relief in the weld seam. Therefore, it is urgent to find a method for judging the impact quality of post-weld welds based on intelligent acoustic information recognition.

Technical Issues

The purpose of the present invention is to provide an intelligent sound-based sound system with accurate recognition and low monitoring cost. The method and system for judging the impact quality of the post-weld weld seam based on information recognition.

Technical Solution

A method for determining the impact quality of a postwelding seam based on smart acoustic information recognition is characterized by comprising the following steps:

S1) controlling a tip of an ultrasonic impact gun to perform impact treatment on the postwelding seam with different treatment pressures, treatment speeds, treatment angles and impact frequencies, acquiring acoustic signals in the impact treatment process, calculating feature values of the acoustic signals, and constructing an acoustic signal sample set including various stress treatment conditions;

S2) determining the impact treatment quality of the postwelding seam, and marking the acoustic signal sample set according to a determination result;

In the determination process, a resistance strain-gage is used as a sensitive element for measurement, and an indentation is made at a center of a strain rosette by impact loading; the strain-gage records the change of strain increment in an elastic area outside an indentation area, so as to obtain a true elastic strain corresponding to a residual stress and further calculate a stress;

a stress relief ratio is calculated by the formula: stress relief ratio=(stress of postwelding seam after impact treatment/stress of postwelding seam before impact treatment)*100%, where the stress of the postwelding seam before impact treatment is a stress of the whole weldment; if the stress relief ratio is higher than 70%, the impact quality is marked as qualified; and if the stress relief ratio is lower than 70%, the impact quality is marked as unqualified;

S3) establishing a multi-weight neural network model, and training the multi-weight neural network model by using the marked acoustic signal sample set marked in S2) to obtain a multi-weight neural network which can be used to determine the impact quality of the postwelding seam;

Step 1: taking four features of each acoustic signal acquired by a training sample acquisition module as a feature vector sample point, labeling them as $A_1$, $A_2$, ..., $A_N$, calculating a distance between any two points in a feature sample set, and storing the distance in an N×N matrix A, where $A_{ij}$ represents a distance between acoustic signal feature sample points $A_i$ and $A_j$, and $A_{ii}$=0 (i=1, 2, ..., N);

Step 2: finding a minimum value in the N×N matrix A, labeling the serial numbers (subscript characters) of two closest acoustic signal feature sample points to be found as $P_{11}$ and $P_{12}$, and constructing a first neuron $\theta_1$ by the two corresponding acoustic signal feature sample points;

Step 3: deleting a point covered by the first neuron $\theta_1$ from the acoustic signal feature sample point set {$A_1$, $A_2$, ..., $A_N$}, calculating a distance from each remaining point to the points $P_{11}$ and $P_{12}$, finding out two points with the shortest distance, labeling them as $P_{21}$ and $P_{22}$, and constructing a second neuron $\theta_2$ of MDOFNN with the acoustic signal feature sample points $P_{21}$ and $P_{22}$;

Step 4: repeating Step 3 on the remaining acoustic signal feature sample points to obtain $P_{i1}P_{i2}$, and constructing an $i^{th}$ neuron $\theta_i$; and Step 5: obtaining N−1 connected neuron line models when i=N−1, meaning that all the points in the acoustic signal feature sample set have been processed;

wherein two multi-weight neuron coverage areas representing "qualified treatment quality" and "unqualified treatment quality" are obtained finally through algorithm iteration, and an Euclidean distance between a test sample and the two multi-weight neuron network coverage areas representing the stress treatment quality of the postwelding seam is calculated; the ones with closer Euclidean distance to the "qualified treatment quality" multi-weight neuron coverage area are the ones with qualified stress treatment quality of the postwelding seam in the test sample, and the ones with closer Euclidean distance to the "unqualified treatment quality" multi-weight neuron coverage area are the ones with unqualified stress treatment quality of the postwelding seam in the test sample;

S4) acquiring feature values of postwelding seam impact treatment acoustic signals to be determined, inputting the feature values into the multi-weight neural network trained in S4), and outputting a judgment result of the impact treatment quality of the postwelding seam to be determined, i.e. judging whether the impact treatment of the postwelding seam to be determined is "qualified treatment quality" or "unqualified treatment quality".

Specifically, S1) comprises: controlling the tip of the ultrasonic impact gun to perform impact treatment on the postwelding seam with different treatment pressures, treatment speeds, treatment angles and impact frequencies; and acquiring acoustic signals in the impact treatment process;

Fourier transform is used to transform the acoustic signals in a time domain into acoustic signals in a frequency domain, and a Butterworth filter is used to filter the acoustic signals in the frequency domain.

After being filtered, the acoustic signals are framed to extract short-time features. A short-time windowing technology is adopted for framing. A Hamming window is adopted, the length of which is 1024, and framing is conducted based on an overlapping rate of 50%.

Then, the short-time zero-crossing rate, short-time average amplitude, short-time energy and short-time zero-energy ratio of the acoustic signals can be extracted from the time domain.

(1) Short-Time Zero-Crossing Rate:

Short-time zero-crossing rate refers to the number of times the signal passes through the zero value in a frame of signals. The formula for calculating the short-time zero-crossing rate $Z_n$ is as follows:

$$Z_n = \frac{1}{2} \sum_{m=n}^{n+N+1} |\text{sgn}[x_\omega(m) - \text{sgn}(x_\omega(m-1))]|$$

wherein represents the current sampling time point, N is the length of the Hamming window, $x_\omega(m)$ represents the windowed signal of x(m), and x(m) the amplitude of the acoustic signal at time m.

(2) Short-Time Energy:

Under different variables, there is a significant energy difference between acoustic signals generated by seam impacting with the ultrasonic impact gun. The formula for calculating the short-time energy $E_n$ is as follows:

$$E_n = \sum_{m=n}^{n+N-1} x_\omega^2(m)$$

(3) Short-Time Average Amplitude:

Short-time energy refers to the sum of squares of acoustic signals in a frame of signals, and short-time average amplitude $M_n$ is used to calculate the sum of absolute values to measure the variation amplitude of the acoustic signals. The formula for calculating the short-time energy $M_n$ is as follows:

$$M_n = \sum_{m=n}^{n+N-1} |x_\omega(m)|$$

(4) Short-Time Zero-Energy Ratio

Short-time zero-energy ratio is the ratio of zero-crossing rate and short-time energy in a frame of signals. The formula for calculating the short-time zero-energy ratio $ZER_n$ is as follows:

$$ZER_n = Zn/E_n.$$

A system for determining the impact quality of a postwelding seam based on smart acoustic information recognition comprises an acoustic signal acquisition hardware platform for acquiring acoustic signals in the process of impact treatment of the postwelding seam; a signal processing and feature extraction module for conducting filtering pretreatment and feature value calculation on the acoustic signals; and a determination module for inputting feature values calculated by the signal processing and feature extraction module into a multi-weight neural network and outputting a quality determination result, wherein the multi-weight neural network is a multi-weight neural network which can be used for determining the impact quality of the postwelding seam after being trained.

The acoustic signal acquisition hardware platform comprises an ultrasonic impact gun, a mobile operation platform, a weldment to be processed, a free-field microphone, a sound and vibration analyzer and a PC, wherein the position of the ultrasonic impact gun is fixed, the weldment to be processed is fixed on the mobile operation platform, and the mobile operation platform can move relative to the ultrasonic impact gun along a length direction of the weldment to be processed. While the mobile operation platform moves together with the weldment to be processed, the ultrasonic impact gun performs seam residual stress treatment on a weld toe of a seam of the weldment to be processed. The free-field microphone is placed in a circle with a radius of 1.5 m centered on a tip of the ultrasonic impact gun, and is used to collect analog signals of sound in the whole treatment process and transmit the analog signals to the sound and vibration analyzer. The sound and vibration analyzer converts the received analog signals of sound into digitized time-domain acoustic signals. Then, the sound and vibration analyzer transmits received sound information to the PC, and the PC stores the information in the form of files. Both the signal processing and feature extraction module and the determination module are arranged in the PC. Then the signal processing and feature extraction module conducts filtering pretreatment and feature value calculation on the acoustic signals. Finally, the determination module inputs calculated feature values into a multi-weight neural network and outputs a quality determination result, and determines whether stress treatment of the postwelding seam to be determined is qualified or not according to the output result.

The signal processing and feature extraction module and the judgment module are set in the PC. The sound vibration analyzer sends the digitized acoustic signal to the PC and stores it in the PC. The signal processing and feature extraction module performs filtering and pre-processing on the acoustic signal. The characteristic value is processed and calculated, and then the acquired characteristic value of the acoustic signal is input to the judgment module, and the judgment module outputs the quality judgment result.

Beneficial Effects

Compared with the prior art, the method for judging the impact quality of post-weld welds based on intelligent acoustic information recognition provided by the present invention extracts features of acoustic signals during ultrasonic stress processing, and uses multi-weight neural network algorithms for pattern recognition. Without damaging the weldment, the stress treatment quality of the welded seam after welding can be quickly and accurately judged, and the cost is low. Greatly improve the reliability of the stress relief process, thereby improving the overall quality of the welding process.

DESCRIPTION OF SEVERAL VIEWS OF THE ATTACHED DRAWINGS

Figure 1:
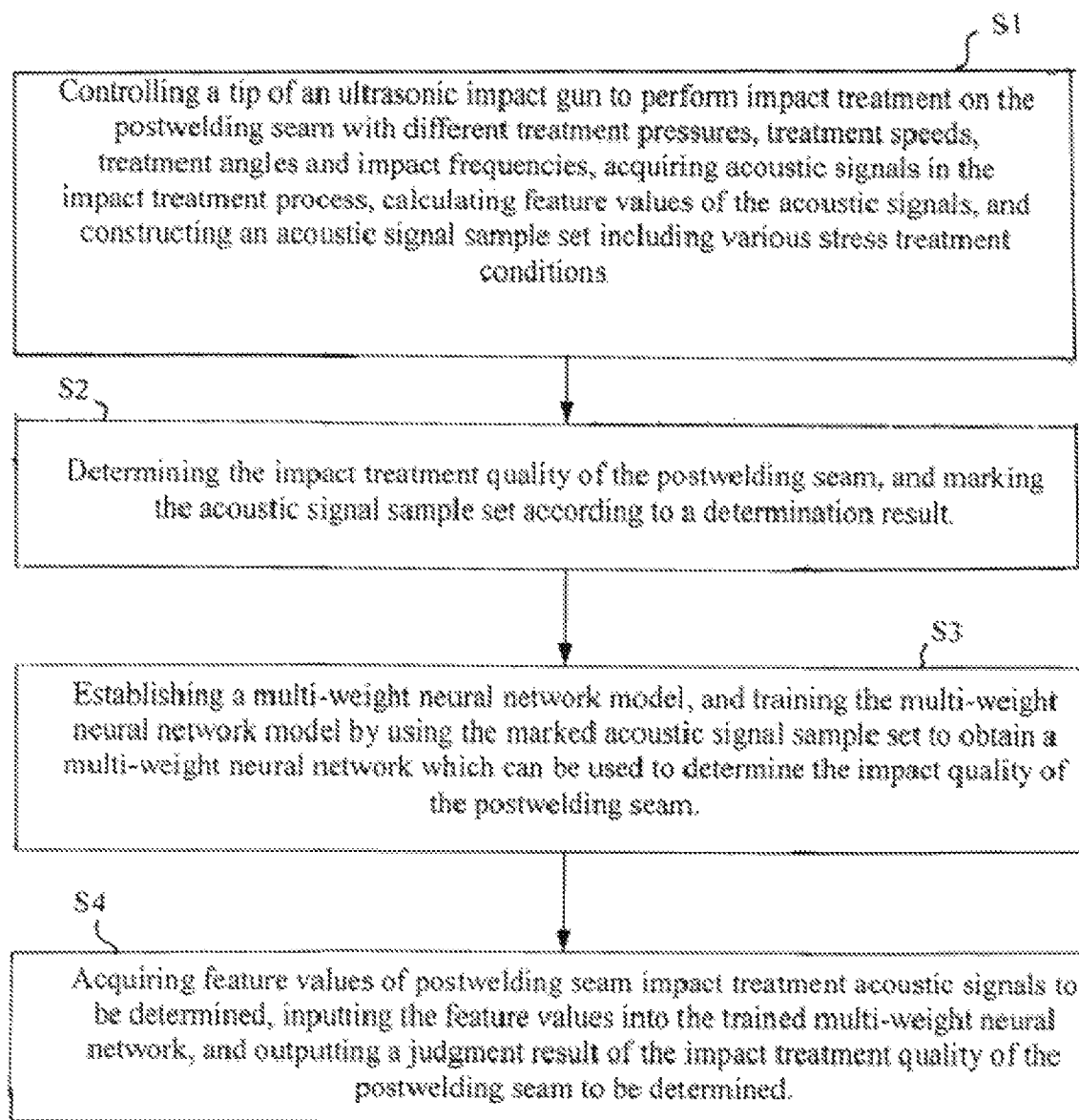
FIG. 1 is a flowchart of a method for determining the impact quality of a postwelding seam based on smart acoustic information recognition provided by the invention.
Figure 2:
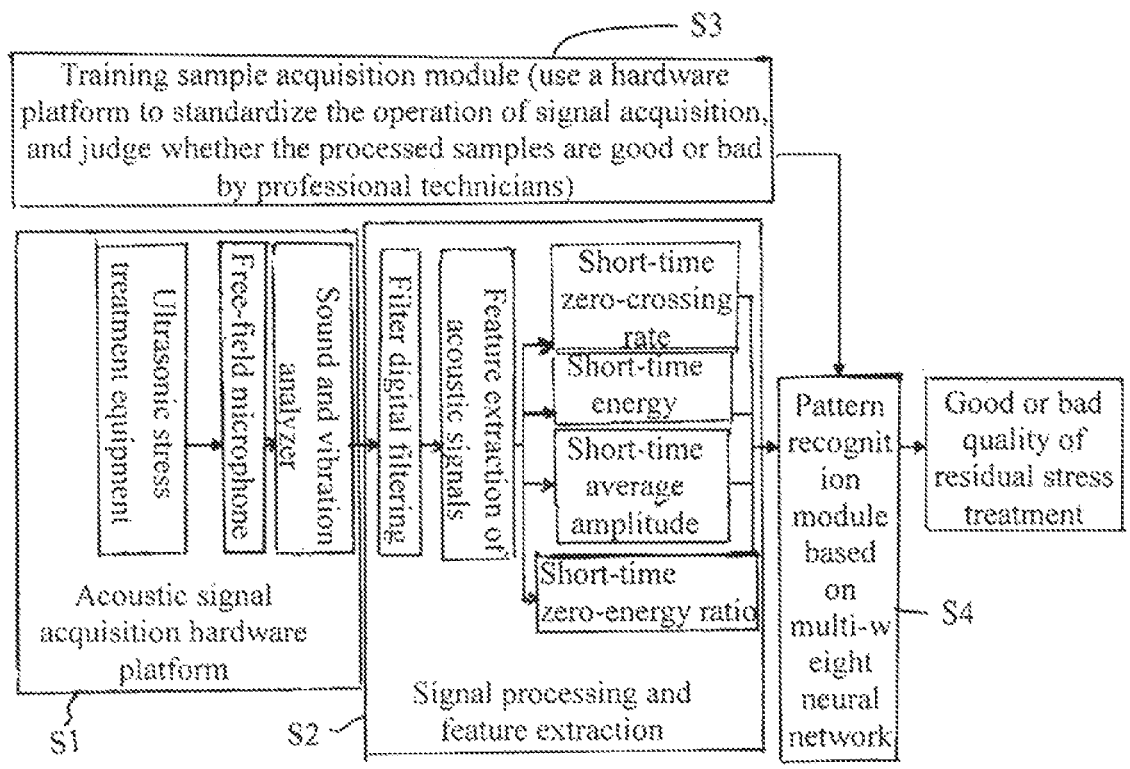
FIG. 2 is a structural diagram of a system for determining the impact quality of a postwelding seam based on smart acoustic information recognition provided by the invention.
Figure 3:
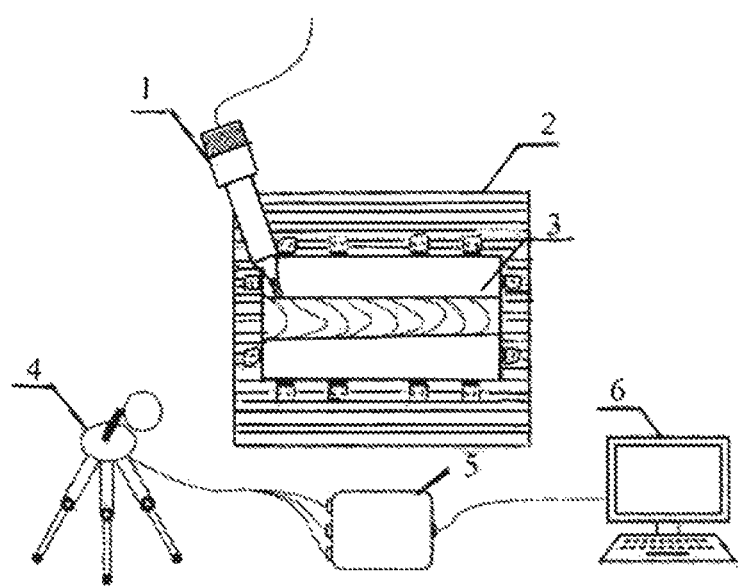
Figure 4:
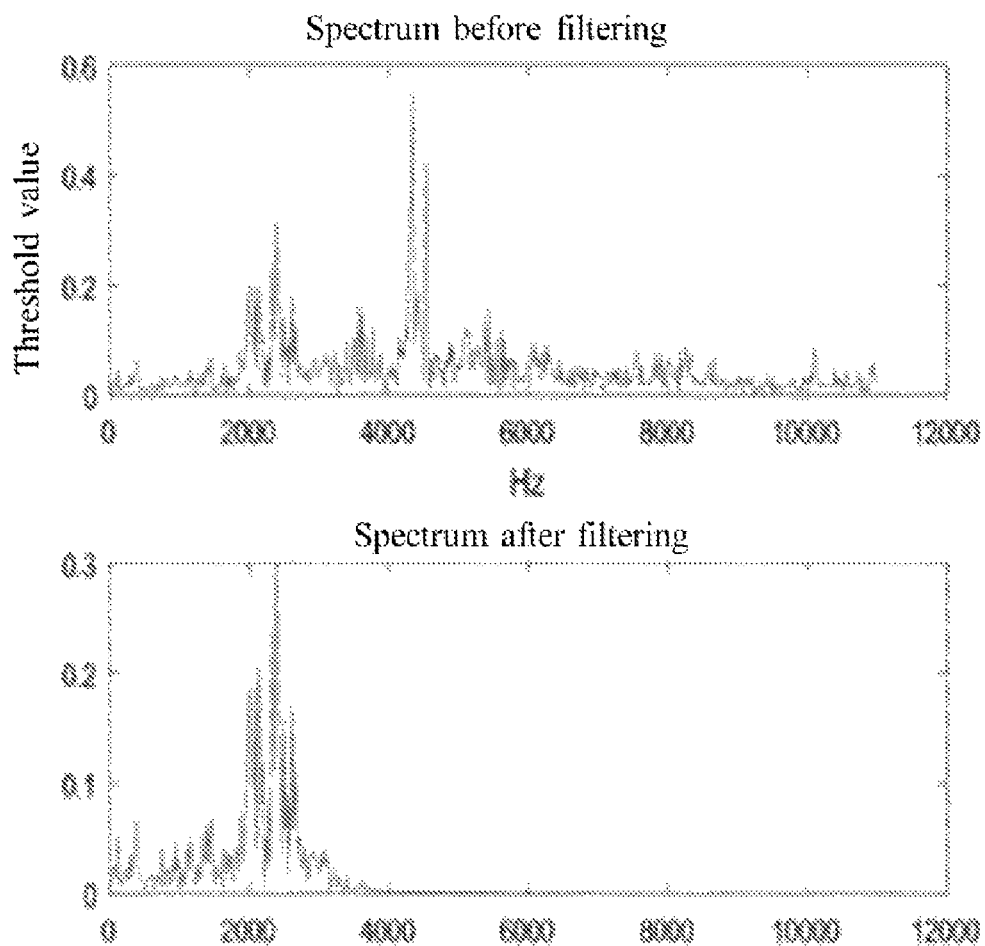

FIG. 3 is a structural diagram of an acoustic signal acquisition hardware platform in a system for determining the impact quality of a postwelding seam based on smart acoustic information recognition provided by the invention; and FIG. 4 is a waveform frequency domain diagram before and after a sound waveform acquired by the acoustic signal acquisition hardware platform is filtered by a Butterworth filter in the invention.

DETAILED DESCRIPTION OF THE INVENTION

A multi-weight neural network can realize the optimal coverage of a complex high-dimensional space. It takes samples as neuron nodes, and constructs hypergeometric bodies to describe a certain type of neurons based on the shortest Euclidean distance, thus forming a complex training space and realizing the function of classified recognition. The multi-weight neural network applied in this patent is composed of two geometric bodies in a high-dimensional space, which respectively represent the qualified and unqualified postwelding stress treatment quality. Each geometric body is constructed with training samples as neuron nodes based on the shortest Euclidean distance between the nodes. A mathematical model of the geometric bodies is set with weight parameters and offset parameters, and can fit the best high-dimensional space coverage according to different training samples and maximize the recognition effect.

A method for determining the impact quality of a postwelding seam based on smart acoustic information recognition is characterized by comprising the following steps:

S1) controlling a tip of an ultrasonic impact gun to perform impact treatment on the postwelding seam with different treatment pressures, treatment speeds, treatment angles and impact frequencies, acquiring acoustic signals in the impact treatment process, calculating feature values of the acoustic signals, and constructing an acoustic signal sample set including various stress treatment conditions;

S2) determining the impact treatment quality of the postwelding seam, and marking the acoustic signal sample set according to a determination result;

wherein the postwelding seam of each processed weldment is measured according to the National Standard of the People's Republic of China Metallic materials—Residual stress determination—The indentation strain-gage method; in the determination process, a resistance strain-gage is used as a sensitive element for measurement, and an indentation is made at a center of a strain rosette by impact loading; the strain-gage records the change of strain increment in an elastic area outside an indentation area, so as to obtain a true elastic strain corresponding to a residual stress and further calculate a stress;

a stress relief ratio is calculated by the formula: stress relief ratio=(stress of postwelding seam after impact treatment/stress of postwelding seam before impact treatment)*100%, where the stress of the postwelding seam before impact treatment is a stress of the whole weldment; if the stress relief ratio is higher than 70%®, the impact quality is marked as qualified; and if the stress relief ratio is lower than 70%, the impact quality is marked as unqualified;

S3) establishing a multi-weight neural network model, and training the multi-weight neural network model by using the marked acoustic signal sample set marked in S2) to obtain a multi-weight neural network which can be used to determine the impact quality of the postwelding seam;

Step 1: taking four features of each acoustic signal acquired by a training sample acquisition module as a feature vector sample point, labeling them as $A_1$, $A_2$, ..., $A_N$, calculating a distance between any two points in a feature sample set, and storing the distance in an N×N matrix A, where $A_{ij}$ represents a distance between acoustic signal feature sample points $A_i$ and $A_j$, and $A_{ii}=0$ (i=1, 2, ..., N);

Step 2: finding a minimum value in the N×N matrix A, labeling the serial numbers (subscript characters) of two closest acoustic signal feature sample points to be found as $P_{11}$ and $P_{12}$, and constructing a first neuron $\theta_1$ by the two corresponding acoustic signal feature sample points;

Step 3: deleting a point covered by the first neuron $\theta_1$ from the acoustic signal feature sample point set $\{A_1, A_2, ..., A_N\}$, calculating a distance from each remaining point to the points $P_{11}$ and $P_{12}$, finding out two points with the shortest distance, labeling them as $P_{21}$ and $P_{22}$, and constructing a second neuron $\theta_2$ of MDOFNN with the acoustic signal feature sample points $P_{21}$ and $P_{22}$;

Step 4: repeating Step 3 on the remaining acoustic signal feature sample points to obtain $P_{i1}P_{i2}$, and constructing an $i^{th}$ neuron $\theta_i$; and Step 5: obtaining N−1 connected neuron line models when i=N−1, meaning that all the points in the acoustic signal feature sample set have been processed;

wherein two multi-weight neuron coverage areas representing "qualified treatment quality" and "unqualified treatment quality" are obtained finally through algorithm iteration, and an Euclidean distance between a test sample and the two multi-weight neuron network coverage areas representing the stress treatment quality of the postwelding seam is calculated; the ones with closer Euclidean distance to the "qualified treatment quality" multi-weight neuron coverage area are the ones with qualified stress treatment quality of the postwelding seam in the test sample, and the ones with closer Euclidean distance to the "unqualified treatment quality" multi-weight neuron coverage area are the ones with unqualified stress treatment quality of the postwelding seam in the test sample; and experiments on several test samples show that the recognition accuracy of the multi-weight neural network can reach 95% or more; and S4) acquiring feature values of postwelding seam impact treatment acoustic signals to be determined, inputting the feature values into the multi-weight neural network trained in S4), and outputting a judgment result of the impact treatment quality of the postwelding seam to be determined, i.e. judging whether the impact treatment of the postwelding seam to be determined is "qualified treatment quality" or "unqualified treatment quality".

Specifically, S1) comprises: controlling the tip of the ultrasonic impact gun to perform impact treatment on the postwelding seam with different treatment pressures (pressure of impact gun tip relative to weld toe), treatment speeds (speed of impact gun tip relative to weld toe), treatment angles (angle of impact gun tip relative to weld toe) and impact frequencies (vibration frequency of piezoelectric ceramic stack) and acquiring acoustic signals in the impact treatment process; for example, controlling the tip of the ultrasonic impact gun to treat the weld toe with the different combinations of treatment pressures of 3 Kg, 4 Kg and 5 Kg, treatment speeds of 16 cm/min and 32 cm/min, treatment angles of 45° and 60°, and impact frequencies of 60% and 85% of the duty ratio of the controller, so as to obtain artificial acoustic signal samples under various stress treatment conditions.

Because the environment in an actual acquisition process is not closed, there must be interference noise in the acquired acoustic signals, which needs to be filtered. Fourier transform is used to transform the acoustic signals in a time domain into acoustic signals in a frequency domain, and a Butterworth filter is used to filter the acoustic signals in the frequency domain. With the largest flat amplitude response, the Butterworth filter can effectively remove high-frequency signals in the acoustic signals in the frequency domain. The amplitude square function is:

$$A((j\omega)^2) = |H_a(j\omega)|^2 = \frac{1}{1+(\omega/\omega_c)^{2N}}$$

where N is the order of the filter and $\omega_c$ is the cut-off frequency of a low-pass filter. The larger the value of N, the more shaking a transition band, and the better the approximation of a passband and a stopband. The Butterworth filter has the advantages of balanced characteristics in attenuation slope, linear phase and loading characteristics, thus being able to effectively remove the high-frequency signals from the acoustic signals in the frequency domain. FIG. 4 is a waveform frequency domain diagram before and after a sound waveform acquired is filtered by the Butterworth filter in the invention.

After being filtered, the acoustic signals are framed to extract short-time features. A short-time windowing technology is adopted for framing. A Hamming window is adopted, the length of which is 1024, and framing is conducted based on an overlapping rate of 50%.

Then, the short-time zero-crossing rate, short-time average amplitude, short-time energy and short-time zero-energy ratio of the acoustic signals can be extracted from the time domain.

(1) Short-Time Zero-Crossing Rate:

Short-time zero-crossing rate refers to the number of times the signal passes through the zero value in a frame of signals. The formula for calculating the short-time zero-crossing rate $Z_n$ is as follows:

$$Z_n = \frac{1}{2}\sum_{m=n}^{n+N+1}|\text{sgn}[x_\omega(m)] - \text{sgn}(x_\omega(m-1))]|$$

where n represents the current sampling time point, N is the length of the Hamming window, $x_\omega(m)$ represents the windowed signal of x(m), and x(m) is the amplitude of the acoustic signal at time m.

(2) Short-Time Energy:

Under different variables, there is a significant energy difference between acoustic signals generated by seam impacting with the ultrasonic impact gun. The formula for calculating the short-time energy $E_n$ is as follows:

$$E_n = \sum_{m=n}^{n+N-1} x_\omega^2(m)$$

(3) Short-Time Average Amplitude:

Short-time energy refers to the sum of squares of acoustic signals in a frame of signals, and short-time average amplitude $M_n$ is used to calculate the sum of absolute values to measure the variation amplitude of the acoustic signals. The formula for calculating the short-time energy $M_n$ is as follows:

$$M_n = \sum_{m=n}^{n+N-1} |x_\omega(m)|$$

(4) Short-Time Zero-Energy Ratio

Short-time zero-energy ratio is the ratio of zero-crossing rate and short-time energy in a frame of signals. The formula for calculating the short-time zero-energy ratio $ZER_n$ is as follows:

$$ZER_n = Z_n/E_n.$$

A system for determining the impact quality of a postwelding seam based on smart acoustic information recognition comprises an acoustic signal acquisition hardware platform for acquiring acoustic signals in the process of impact treatment of the postwelding seam; a signal processing and feature extraction module for conducting filtering pretreatment and feature value calculation on the acoustic signals; and a determination module for inputting feature values calculated by the signal processing and feature extraction module into a multi-weight neural network and outputting a quality determination result, wherein the multi-weight neural network is a multi-weight neural network which can be used for determining the impact quality of the postwelding seam after being trained.

The acoustic signal acquisition hardware platform comprises an ultrasonic impact gun 1, a mobile operation platform 2, a weldment to be processed 3, a free-field microphone 4, a sound and vibration analyzer 5 and a PC 6, wherein the position of the ultrasonic impact gun 1 is fixed, the weldment to be processed 3 is fixed on the mobile operation platform 2, and the mobile operation platform 2 can move relative to the ultrasonic impact gun 1 along a length direction of the weldment to be processed 3. While the mobile operation platform 2 moves together with the weldment to be processed 3, the ultrasonic impact gun 1 performs seam residual stress treatment on a weld toe of a seam of the weldment to be processed 3. The free-field microphone 4 is placed in a circle with a radius of 1.5 m centered on a tip of the ultrasonic impact gun 1, and is used to collect analog signals of sound in the whole treatment process and transmit the analog signals to the sound and vibration analyzer 5. The sound and vibration analyzer 5 converts the received analog signals of sound into digitized time-domain acoustic signals. Then, the sound and vibration analyzer 5 transmits received sound information to the PC 6, and the PC 6 stores the information in the form of files. Both the signal processing and feature extraction module and the determination module are arranged in the PC 6. Then the signal processing and feature extraction module conducts filtering pretreatment and feature value calculation on the acoustic signals. Finally, the determination module inputs calculated feature values into a multi-weight neural network and outputs a quality determination result, and determines whether stress treatment of the postwelding seam to be determined is qualified or not according to the output result. By using the system to judge the quality of stress relief treatment, the stress treatment quality of the postwelding seam can be quickly and accurately judged without damaging the weldment, and the cost is low.

What is claimed is:

1. A method for determining a smart acoustic information recognition-based welded weld impact quality, comprising the following steps:
    S1) controlling a tip of an ultrasonic impact gun to perform impact treatment on a postwelding seam with different treatment pressures, treatment speeds, treatment angles and impact frequencies, acquiring acoustic signals in the impact treatment process, calculating feature values of the acoustic signals, and constructing an acoustic signal sample set including various stress treatment conditions;
    S2) determining an impact treatment quality of the postwelding seam, and marking the acoustic signal sample set according to a determination result;
    in a determination process, a resistance strain-gage is used as a sensitive element for measurement, and an indentation is made at a center of a strain rosette by impact loading; the strain-gage records the change of strain increment in an elastic area outside an indentation area, obtaining a true elastic strain corresponding to a residual stress and further calculating a stress;
    a stress relief ratio is calculated by a formula: stress relief ratio=(stress of postwelding seam after impact treatment/stress of postwelding seam before impact treatment)*100%, where the stress of the postwelding seam before impact treatment is a stress of the whole weldment; if the stress relief ratio is higher than 70%, the impact quality is marked as qualified; and if the stress relief ratio is lower than 70%, the impact quality is marked as unqualified;
    S3) establishing a multi-weight neural network model, and training the multi-weight neural network model by using the marked acoustic signal sample set marked in S2) to obtain a multi-weight neural network which is used to determine the impact quality of the postwelding seam;
        step 1: taking four features of each acoustic signal acquired by a training sample acquisition module as a feature vector sample point, labeling them as $A_1, A_2, \ldots, A_N$, calculating a distance between any two points in a feature sample set, and storing the distance in an N×N matrix A, where $A_{ij}$ represents a distance between acoustic signal feature sample points $A_i$ and $A_j$, and $A_{ii}=0$ (i=1, 2, ..., N);
        step 2: finding a minimum value in the N×N matrix A, labeling the serial numbers (subscript characters) of two closest acoustic signal feature sample points to be found as $P_{11}$ and $P_{12}$, and constructing a first neuron $\theta_1$ by the two corresponding acoustic signal feature sample points;
        step 3: deleting a point covered by the first neuron $\theta_1$ from the acoustic signal feature sample point set $\{A_1, A_2, \ldots, A_N\}$, calculating a distance from each remaining point to the points $P_{11}$ and $P_{12}$, finding out two points with the shortest distance, labeling them as $P_{21}$ and $P_{22}$, and constructing a second neuron $\theta_2$ of MDOFNN with the acoustic signal feature sample points $P_{21}$ and $P_{22}$;
        step 4: repeating step 3 on the remaining acoustic signal feature sample points to obtain $P_{i1}P_{i2}$, and constructing an $i^{th}$ neuron $\theta_i$; and
        step 5: obtaining N−1 connected neuron line models when i=N−1, meaning that all the points in the acoustic signal feature sample set have been processed;
    wherein two multi-weight neuron coverage areas representing "qualified treatment quality" and "unqualified treatment quality" are obtained finally through algorithm iteration, and an Euclidean distance between a test sample and the two multi-weight neuron network coverage areas representing a stress treatment quality of the postwelding seam is calculated; the ones with closer Euclidean distance to the "qualified treatment quality" multi-weight neuron coverage area are the ones with qualified stress treatment quality of the postwelding seam in the test sample, and the ones with closer Euclidean distance to the "unqualified treatment quality" multi-weight neuron coverage area are the ones with unqualified stress treatment quality of the postwelding seam in the test sample;
    S4) acquiring feature values of postwelding seam impact treatment acoustic signals to be determined, inputting the feature values into the multi-weight neural network trained in S3), and outputting a judgment result of the impact treatment quality of the postwelding seam to be determined, wherein judging whether the impact treatment of the postwelding seam is "qualified treatment quality".

2. The method according to claim 1, wherein in the step S1), further comprises:
    controlling the tip of the ultrasonic impact gun to perform impact treatment on the postwelding seam with different treatment pressures, treatment speeds, treatment angles and impact frequencies; and acquiring acoustic signals in the impact treatment process;

Fourier transform is used to transform the acoustic signals in a time domain into acoustic signals in a frequency domain, and a Butterworth filter is used to filter the acoustic signals in the frequency domain;

after being filtered, the acoustic signals are framed to extract short-time features;

a short-time windowing technology is adopted for framing; a Hamming window is adopted, the length of which is 1024, and framing is conducted based on an overlapping rate of 50%;

then, the short-time zero-crossing rate, short-time average amplitude, short-time energy and short-time zero-energy ratio of the acoustic signals can be extracted from the time domain;

(1) short-time zero-crossing rate:

short-time zero-crossing rate refers to number of times the signal passes through the zero value in a frame of signals; formula for calculating the short-time zero-crossing rate $Z_n$ is as follows:

$$Z_n = \frac{1}{2}\sum_{m=n}^{n+N+1} |\text{sgn}[x_\omega(m) - \text{sgn}(x_\omega(m-1))]|$$

where n represents the current sampling time point, N is the length of the Hamming window, $x_\omega(m)$ represents the windowed signal of x(m), and x(m) is the amplitude of the acoustic signal at time m;

(2) short-time energy:

under different variables, there is a significant energy difference between acoustic signals generated by seam impacting with the ultrasonic impact gun;

a formula for calculating the short-time energy $E_n$ is as follows:

$$E_n = \sum_{m=n}^{n+N-1} x_\omega^2(m)$$

(3) short-time average amplitude:

short-time energy refers to sum of squares of acoustic signals in a frame of signals, and short-time average amplitude $M_n$ is used to calculate sum of absolute values to measure a variation amplitude of the acoustic signals; a formula for calculating the short-time energy $M_n$ is as follows:

$$M_n = \sum_{m=n}^{n+N-1} |x_\omega(m)|$$

(4) short-time zero-energy ratio short-time zero-energy ratio is the ratio of zero-crossing rate and short-time energy in a frame of signals; the formula for calculating the short-time zero-energy ratio $ZER_n$ is as follows:

$$ZER_n = Z_n/E_n.$$

3. A system for determining the impact quality of a postwelding seam based on the smart acoustic information recognition-based welded weld impact quality determination method according to claim 1, comprising an acoustic signal acquisition hardware platform for acquiring acoustic signals in the process of impact treatment of the postwelding seam; a signal processing and feature extraction module for conducting filtering pretreatment and feature value calculation on the acoustic signals; and a determination module for inputting feature values calculated by the signal processing and feature extraction module into a multi-weight neural network and outputting a quality determination result, wherein the multi-weight neural network is a multi-weight neural network which is used for determining the impact quality of the postwelding seam after being trained; wherein the acoustic signal acquisition hardware platform comprises an ultrasonic impact gun, a mobile operation platform, a weldment to be processed, a free-field microphone, a sound and vibration analyzer and a PC, wherein a position of the ultrasonic impact gun is fixed, the weldment to be processed is fixed on the mobile operation platform, and the mobile operation platform moving relative to the ultrasonic impact gun along a length direction of the weldment to be processed; while the mobile operation platform moving together with the weldment to be processed, the ultrasonic impact gun performs seam residual stress treatment on a weld toe of a seam of the weldment to be processed; the free-field microphone is placed in a circle with a radius of 1.5 m centered on a tip of the ultrasonic impact gun, and is used to collect analog signals of sound in the whole treatment process and transmit the analog signals to the sound and vibration analyzer; the sound and vibration analyzer converting the received analog signals of sound into digitized time-domain acoustic signals; then, the sound and vibration analyzer transmits received sound information to the PC, and the PC storing the information in the form of files; both the signal processing and feature extraction module and the determination module are arranged in the PC; then the signal processing and feature extraction module conducts filtering pretreatment and feature value calculation on the acoustic signals; finally, the determination module inputting calculated feature values into a multi-weight neural network and outputs a quality determination result, and determining whether stress treatment of the postwelding seam is qualified according to the output result.

* * * * *